United States Patent [19]

de Wied

[11] Patent Number: 4,487,765
[45] Date of Patent: Dec. 11, 1984

[54] PEPTIDES

[75] Inventor: David de Wied, Bilthoven, Netherlands

[73] Assignee: Akzo N.V., Arnhem, Netherlands

[21] Appl. No.: 542,774

[22] Filed: Oct. 17, 1983

[30] Foreign Application Priority Data

Oct. 13, 1982 [NL] Netherlands ........................ 8203949
Dec. 17, 1982 [NL] Netherlands ........................ 8204881

[51] Int. Cl.³ ..................... A61K 37/00; C07C 103/52
[52] U.S. Cl. ............................... 424/177; 260/112.5 R
[58] Field of Search ................... 260/112.5 R; 424/177

[56] References Cited

PUBLICATIONS

Perspectives in Peptide Chemistry by Greven and de Wied, Switzerland, 1981, pp. 356-371, Neuropeptides and Behaviour.

Neurohypophyseal Peptides Hormones and Other Biologically Active Peptides by Burbach and de Wied, Holland, 1981, pp. 69-87, Memory Effects and Brain Proteolysis of Neurohypophyseal Hormones.

Primary Examiner—Delbert R. Phillips
Attorney, Agent, or Firm—Abelman, Frayne, Rezac & Schwab

[57] ABSTRACT

The present invention relates to peptides with psychopharmacological properties of the formula

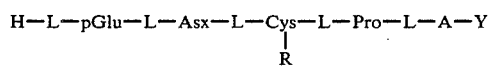

wherein
R represents

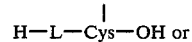

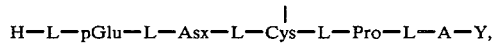

A represents the amino acid residue Arg, Lys or Leu and
Y represents the group OH or the group Gly-OH, as well as functional derivatives thereof.

4 Claims, No Drawings

PEPTIDES

The present invention relates to peptides having psychopharmacological properties, to a process for the preparation of these peptides and to a pharmaceutical formulation which contains these peptides as the active ingredient.

More especially, the invention relates to peptides which in the main are to be regarded as fragments of vasopressin and oxytocin.

Both oxytocin and vasopressin are peptides which apart from their hormonal effects are also described as neuropeptides, namely as peptides which inter alia effect memory processes.

We have now found peptides which do no longer exert the hormonal effects of oxytocin and vasopressin but which have a greater and more specific influence on memory processes.

The present invention relates to peptides having the general formula I:

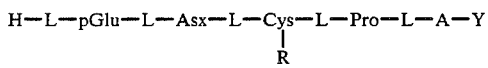

wherein
R represents

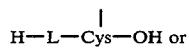

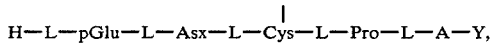

A represents the amino acid residue Arg, Lys or Leu and Y represents the group OH or the group Gly-OH, as well as the functional derivative thereof.

The peptides and peptide derivatives according to formula I are prepared in the manner conventional for peptides. A conventional process for the preparation of the present compounds is to couple the required amino acids by condensation, either in a homogeneous phase or employing a so-called solid phase.

The condensation in the homogeneous phase can be carried out as follows:
(a) condensation of an amino acid or peptide, having a free carboxyl group and protected other reactive groups, with an amino acid or peptide having a free amino group and protected other reactive groups, in the presence of a condensation agent,
(b) condensation of an amino acid or peptide having an activated carboxyl group and, optionally, protected other reactie groups, with an amino acid or peptide having a free amino group and, optionally, protected other reactive groups, or
(c) condensation of an amino acid or peptide having a free carboxyl group and protected other reactive groups, with an amino acid or peptide having an activated amino group and, optionally, protected other reactive groups.

The activation of the carboxyl group can inter alia take place by converting the carboxyl group to an acid halide, an azide, an anhydride, an imidazolide or an activated ester, such as the N-hydroxy-succinimide, N-hydroxy-benztriazole or p-nitrophenyl ester.

The amino group can be activated by converting it to a phosphite amide or by employing the "phosphorazo" method.

The commonest methods for the above condensation reactions are: the carbodiimide method, the azide method, the mixed anhydride method and the method of activated esters, as described in "The Peptides", volume I, 1965 (Academic Press), E. Schröder and K. Lübke.

However, it is also possible to prepare compounds according to formula I by the "solid phase" method of Merrifield, described in J.Amer.Chem.Soc. 85, 2149 (1963). The coupling of the amino acids of the peptides to be prepared starts from the carboxy-terminal side. For this, a solid carrier is necessary, on which reactive groups are present or to which such groups can be attached. This carrier can be, for example, a copolymer of benzene and divinylbenzene having reactive chloromethyl groups, or a polymeric carrier which has been rendered reactive with hydroxymethyl or benzylamine.

If, for example, a carrier containing chloromethyl groups is employed, the bonding of the first α-amino-protected amino acid to the carrier takes place via an ester bond. In the synthesis of the peptide according to formula I wherein Y represents Gly-OH, this reaction thus in the first instance gives:

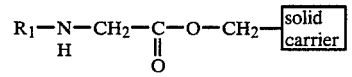

wherein $R_1$ is an α-amino-protective group.

After removal of the group $R_1$, the subsequent α-amino-protected amino acid (in this case, for example, lysine, of which the ε-amino group is also protected) can be coupled by a condensation reaction, and after deprotecting the α-amino group the next amino acid can be coupled, etc. In most cases, it is preferred to have a considerable excess of each α-amino-protected amino acid in the reaction medium, which medium furthermore, in addition to the solid carrier, contains, for example, methylene chloride or a mixture of dimethylformamide and methylene chloride.

After synthesis of the desired amino acid sequence, the peptide is released from the carrier by, for example, HF or trifluoromethanesulphonic acid. The peptide can also be removed from the carrier by trans-esterification with a lower alcohol, preferably methanol or ethanol, directly resulting in a lower alkyl ester of the peptide. Similarly, splitting using ammonia gives the amide.

The reactive groups which are not to participate in the condensation reaction are protected by groups which can again very easily be removed, for example by hydrolysis or reduction. Thus, a carboxyl group can be protected effectively by, for example, esterification with methanol, ethanol, tertiary butanol, benzyl alcohol or p-nitrobenzyl alcohol.

Groups which can effectively protect an amino group are usually acid groups, for example an acid group derived from an aliphatic, aromatic, araliphatic or heterocyclic carboxylic acid, such as acetic acid, benzoic acid or pyridinecarboxylic acid, or an acid group derived from carbonic acid, such as the ethoxycarbonyl, benzyloxycarbonyl, t-butoxycarbonyl or p-methoxy-benzyloxycarbonyl group, or an acid group derived from a sulphonic acid, such as the benzenesulphonyl or p-toluenesulphonyl group, but other groups can also be used, such as substituted or unsubstituted aryl or aralkyl groups, for example benzyl and triphenylmethyl groups, or groups such as ortho-nitrophenylsulphenyl and 2-benzoyl-1-methylvinyl.

It is advisable also to protect the ε-amino group of lysine and the guanidine group of arginine. Conventional protective groups in this context are, for lysine, a tertiary-butoxycarbonyl group or a tosyl group, and for arginine a nitro or Mbs group.

Although in the above-mentioned amino acid condensations the amino acid cystine can be employed, it is preferable to use, in the first instance, the amino acid cysteine, wherein the thiol group (—SH) is protected by means of a conventional SH-protective group, such as acetamidomethyl or trityl. After the final desired amino acid sequence (with cysteinyl in place of cystinyl) has been built up, the thiol group of the cysteinyl residue present in the peptide is then coupled in a known manner (where appropriate after removal of the thiol-protective group) to the thiol group of a second cysteine molecule or to the thiol group of a second molecule of the same peptide.

The N-terminal amino acid pGlu in the peptide according to the invention can be obtained by employing the amino acid pyroglutamic acid in the amino acid condensations. However, it is preferable to synthesize the desired peptide by using glutamine (in place of pyroglutamic acid) and to convert the glutaminyl group of the peptide thus prepared, in a generally known manner, to a pyroglutamic acid residue after the condensation reactions have taken place, and to remove the protective groups used.

The protective groups can be split off by various conventional methods, depending on the type of the group concerned, for example by means of trifluoroacetic acid or methanesulphonic acid.

By functional derivatives of the peptides according to the general formula I there are to be understood:
1. salts of the present peptides, in particular the acid addition salts and metal salts;
2. N-acyl derivatives derived from an aliphatic carboxylic acid having 1-6 carbon atoms, and preferably acetic acid;
3. amides or monoalkyl- or dialkyl-substituted amides, alkyl having 1-6 carbon atoms;
4. esters derived from alcohols having 1-18 C atoms and preferably from aliphatic alcohols having 1-6 C atoms.

The acid addition salts can be obtained directly by isolating the peptide from the desired acid medium; alternatively the peptide obtained can subsequently be converted to an acid addition salt by reaction of the peptide with an acid such as HCl, HBr, phosphoric acid, sulphuric acid, acetic acid, maleic acid, tartaric acid, citric acid or polyglutamic acid.

The metal salts, in particular the alkali metal salts, are obtained by reacting the peptide with the desired metal base, such as NaOH, Na$_2$CO$_3$, NaHCO$_3$ etc. or, in the "solid phase" method, by splitting the peptide-carrier bond with an alkali metal hydroxide.

N-Acyl derivatives, by which there are in particular meant the N-terminal acyl derivatives, are preferably prepared by employing, in the peptide synthesis, an amino acid which is already provided with the relevant acyl group. This acyl group then also functions as a protective group in the peptide synthesis. The desired acyl derivative is in this way prepared directly. However, it is also possible to introduce the desired acyl group subsequently by acylating the peptide in the conventional manner.

The N-acyl group preferentially employed is the acetyl group.

In the homogeneous condensation method esters and amides of the peptides according to formula I are also preferably prepared by employing in the peptide synthesis, an amino acid which is already provided with the desired ester or amide group. They can however also be prepared by subsequently, in the conventional manner, esterifying the peptide obtained or converting it to an amide. In the "solid phase" method, esters can be obtained by transesterification of the peptide-carrier bond and amides can be obtained by treatment with ammonia.

Preferably, the lower aliphatic esters derived from an alcohol having 1-6 C atoms are employed, such as the methyl, ethyl, propyl, isopropyl, butyl, sec.-butyl, pentyl or hexyl esters.

Amides which are preferentially employed are the unsubstituted amide, the monomethylamide or dimethylamide, or the monoethylamide or diethylamide.

The peptides according to the invention have, as already mentioned above, a psychopharmacological effect and in particular exert an influence on memory processes; this influence is significantly and strikingly greater than that of known neuropeptides such as oxytocin and vasopressin.

Peptides according to the present invention, wherein A represents Lys or Arg, greatly promote the consolidation of memory and are in general to be used in cases where a stimulation of mental performance is desired, such as in the treatment of depressions, but in particular in the treatment of disturbances of the learning processes and memory processes, such as can for example occur in older people (senility).

Peptides according to the invention wherein A represents Leu inhibit the consolidation of and retrieval from the memory. These peptides are in general therefore to be employed in cases where inhibition of the central nervous system is desired; they can in general be used, for example, in the treament of obsession neuroses and other forms of inadequate behaviour.

Preferred peptides of the formula I are peptides wherein Asx represents asparaginyl.

The peptides according to the invention can be administered orally, rectally, parenterally, sublingually or intranasally. Parenteral and intranasal administrations are to be preferred. The peptides are therefore preferably mixed with pharmaceutically acceptable auxiliaries which make the peptides suitable for parenteral or intranasal administration, resulting in solutions, suspensions (where appropriate via micro-encapsulation), emulsions and sprays.

Mixed with suitable auxiliaries the present peptides can also be employed in a form which is suitable for oral administration, such as pills, tablets and dragees. The present peptides can also be administered in the form of a suppository.

The peptides or peptide derivatives according to the invention are preferably employed in dosages of 1 ng to 5 μg per kg of body weight per day for parenteral or intranasal administration. The recommended dosage for administration to man is between 1 and 100 μg per day. For oral and rectal administration the dosage is in general greater by a factor of 10-100.

The following is to be noted with respect to the examples which follow.

I. Where no optical configuration is mentioned, the L-form is meant.

II. The following abbreviations are used for the protective or activating groups employed:

Scm = S-carbomethoxysulphenyl
tBu = tertiary butyl
Me = methyl
Mbs = 4-methoxybenzenesulphonyl
Z = benzyloxycarbonyl
Trt = trityl.

III. The following abbreviations are used for the solvents or reagents employed:

EtOH = ethanol
BuOH = butanol
Py = pyridine
HOAc = acetic acid
Am = amyl alcohol
t.-BuOH = tert.-butanol
EtAc = ethyl acetate
MeOH = methanol
DCHA = dicyclohexylamine
DMF = dimethylformamide
THF = tetrahydrofuran
DCC = dicyclohexylcarbodiimide
DCU = dicyclohexylurea
TFA = trifluoroacetic acid
N.E.M. = N-ethylmorpholine
HOBt = N-hydroxybenztriazole IV. The following abbreviations are used for the amino acid groups:

Lys = lysyl
Gly = glycyl
Arg = arginyl
Pro = prolyl
Cys = cysteinyl
Asx = aspartyl or asparaginyl
Asp = aspartyl
Asn = asparaginyl
Glu = glutamyl
Gln = glutaminyl
pGlu = pyroglutamyl.

EXAMPLE 1

1. Z-Arg(Mbs)-OtBu 42.5 g (59.01 millimols) of Z-Arg(Mbs)-OH.DCHA are suspended in 500 ml of EtAc and 150 ml of $H_2O$, in which 9.97 g (73.21 millimols) of $KHSO_4$ had been dissolved. After all the material had dissolved, the layers were separated and the organic layer was washed with 100 ml of 30% strength NaCl solution. The organic layer was dried over $Na_2SO_4$ and then evaporated down. 135 ml of isobutene were condensed at $-30°$ C., after which a solution of Z-Arg(Mbs)-OH in 400 ml of $CH_2Cl_2$ and 5 ml of concentrated $H_2SO_4$ was added. The mixture was stirred for 4 days, after which the isobutene was evaporated off. The organic layer was introduced into a separating funnel, after which water was added, with sufficient $Na_2CO_3$ that the pH became 7. The layers were subsequently separated and the organic layer was washed with $3 \times 100$ ml of 5% strength $NaHCO_3$, 5% strength $KHSO_4$ and 30% strength NaCl solution. The organic layer was dried over $Na_2SO_4$. After addition of petroleum ether, a precipitate formed, which was filtered off and washed with petroleum ether.

Yield: 18.61 g (59.0%).
Rf in $CHCl_3$:MeOH (8:2) = 0.84 ($SiO_2$).

2. H-Arg(Mbs)-OtBu 18.00 g of Z-Arg(Mbs)-OtBu, in 180 ml of MeOH, were hydrogenated with 5% strength Pd/C and hydrogen. Thereafter the Pd/C was filtered off and the solution was evaporated down. The residue (froth) was again evaporated and dissolved in 200 ml of EtAc, and the solid which did not dissolve was filtered off. The filtrate was then evaporated down until a froth was left.

Yield: 12.72 g (93%).
Rf in $CHCl_3$:MeOH:$H_2O$ (70:30:5) = 0.63 ($SiO_2$).

3. Z-Pro-Arg(Mbs)-OtBu 5.15 g (38.11 millimols) of HOBt and 7.23 g (34.94 millimols) of DCC were added successively to a mixture of 12.72 g (31.76 millimols) of H-Arg(Mbs)-OtBu and 7.92 g (31.76 millimols) of Z-Pro-OH at $-5°$ C. Thereafter the mixture was stirred for 15 minutes at $-5°$ C., 45 minutes at $0°$ C. and overnight at room temperature. The DCU was filtered off and the solution was evaporated. Thereafter, the oil which remained was dissolved in 500 ml of ethyl acetate, and the solution was then extracted with $3 \times 100$ ml of 5% strength $KHSO_4$, 5% strength $NaHCO_3$ and water. The organic layer was dried with $Na_2SO_4$ and then evaporated down. The oil obtained was then dissolved in methanol. An oil-like product was obtained by adding water.

Yield: 16.75 g (85.9%).
Rf in toluene:EtOH (8:2) = 0.40 ($SiO_2$).

4. Z-Pro-Arg(Mbs)-OH 15 g (23.74 millimols) of Z-Pro-Arg(Mbs)-OtBu were dissolved in 150 ml of 90% strength TFA and 1.5 ml of anisole and the mixture was stirred for 1 hour. Thereafter, the reaction mixture was introduced into 1,500 ml of ether, causing an oil to separate out. The supernatant liquid was subsequently decanted and the oil was stirred with ether. The ether was decanted. The oil was then dissolved in 100 ml of $CH_2Cl_2$ and added dropwise to ether, resulting in a precipitate. The precipitate was filtered off and dried over KOH.

Yield: 12.51 g (91.5%).
Rf in $CH_2Cl_2$:MeOH:water (70:30:5) = 0.46 ($SiO_2$).

5. Z-Pro-Arg(Mbs)-Gly-$NH_2$

A solution of 2.54 g (22.94 millimols) of H-Gly-$NH_2$:HCl in 25 ml of DMF, to which 2.89 ml (22.94 millimols) of NEM had been added, was added to a mixture of 12 g (20.85 millimols) of Z-Pro-Arg(Mbs)-OH and 5.64 g (41.70 millimols) of HOBt in 180 ml of DMF at $-10°$ C. 4.75 g (22.95 millimols) of DCC were added to this reaction mixture at $-10°$ C. The mixture was then stirred for 1 hour at $-10°$ C. and overnight at $4°$ C. Thereafter, the DCU was filtered off and the filtrate was evaporated until an oil was obtained. The latter was dissolved in 200 ml of a mixture of 2-BuOH in $CH_2Cl_2$ (2:3) and extracted with $3 \times 50$ ml of 5% strength $KHSO_4$, 5% strength $NaHCO_3$ and 30% strength NaCl solution. The organic layer was then dried over $Na_2SO_4$. Petroleum ether was added to the organic layer, resulting in a precipitate. The precipitate was filtered off and washed with petroleum ether.

Yield: 94.3% = 12.42 g.
Rf in $CHCl_3$:MeOH:$H_2O$ (70:30:5) = 0.77 ($SiO_2$).

6. Trt-Cys(Trt)-Pro-Arg(Mbs)-Gly-NH₂

1.75 g (2.77 millimols) of Z-Pro-Arg(Mbs)-Gly-NH₂ in 50 ml of DMF were hydrogenated with H₂ and 5% strength Pd/C. The Pd/C was filtered off and the mixture was cooled to −10° C., after which 1.35 g (2.71 millimols) of Trt-Cys(Trt)-OH, 0.70 g (5.16 millimols) of HOBt and 0.59 g of DCC were added successively. The mixture was then stirred for 15 minutes at −10° C., then for 1 hour at 0° C., and thereafter overnight at room temperature. The reaction mixture was cooled to −25° C., the DCU formed was filtered off and the filtrate was evaporated to leave an oil. This oil was dissolved in 50 ml of a mixture of 2-BuOH and CH₂Cl₂ (2:3) and extracted with 3×15 ml of 5% strength NaHCO₃, 5% strength KHSO₄ and 30% strength NaCl solution. The organic layer was dried over Na₂SO₄ and evaporated down.

Yield: 2.70 g (96%).
Rf in CHCl₃:MeOH:H₂O (70:30:5)=0.82 (SiO₂).

7. H-Cys(Trt)-Pro-Arg(Mbs)-Gly-NH₂

6.85 g (6.31 millimols) of Trt-Cys(Trt)-Pro-Arg(Mbs)-Gly-NH₂ were dissolved in 40 ml of acetic acid. 4 ml of water were added slowly to this solution. After the solution had been stirred for a further hour at room temperature, a further 40 ml of water were added, resulting in a precipitate. This precipitate was filtered off, the filtrate was evaporated to give an oil, and the oil was dissolved in 70 ml of 2-BuOH:CH₂Cl₂ (2:3) and extracted with 3×10 ml of 5% strength NaHCO₃ and 3×10 ml of 30% strength NaCl solution. The organic layer was dried over Na₂SO₄. Addition of ether resulted in a precipitate which was filtered off and dried.

Yield: 5.08 g (89%).
Rf in CHCl₃:MeOH:H₂O (70:30:5)=0.71 (SiO₂).

8. Z-Gln-Asn-Cys(Trt)-Pro-Arg(Mbs)-Gly-NH₂

0.66 g (4.87 millimols) of HOBt and 0.85 g (4.10 millimols) of DCC were added successively to a solution of 3.42 g (4.06 millimols) of the peptide obtained in 7. and 1.60 g (4.06 millimols) of Z-Gln-Asn-OH in 50 ml of DMF at −10° C. After the solution had been stirred for 24 hours, it was cooled to −25° C. and the DCU formed was filtered off. The filtrate was poured out into 100 ml of 5% strength NaHCO₃, resulting in a precipitate. The precipitate was filtered off and washed 3 times with water and then dried.

Yield: 4.0 g (80.8%).
Rf in CH₂Cl₂:MeOH:H₂O (70:30:5)=0.70 (SiO₂).

9. Z-Gln-Asn-Cys(Scm)-Pro-Arg-Gly-NH₂

4.0 g (3.23 millimols) of the peptide obtained in 8. were dissolved in 100 ml of methanol and 100 ml of CH₂Cl₂. Thereafter, 0.6 ml of S-carboxymethylsulphenyl chloride was added. After the mixture had been stirred for 1 hour, the precipitate formed was filtered off and washed with ether.

Yield: 2.00 g (57%).
Rf in CH₂Cl₂:MeOH:H₂O (70:30:5)=0.55 (SiO₂).

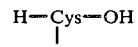

10. Z—Gln—Asn—Cys—Pro—Arg(Mbs)—Gly—NH₂.HCl 2.00 g (1.84 millimols) of the peptide obtained in 9. were dissolved in 100 ml of methanol, after which 0.65 g (3.68 millimols) of H.Cys-OH.HCl.H₂O were added. The mixture was stirred for 1 hour, after which 100 ml of ether were added, and a precipitate was formed. The liquid was decanted and the crystals were stirred twice with ether. The residue was then dissolved in a very small amount of methanol and purified by chromatography.

Yield: 650 mg (31.3%).
Rf in BuOH:HOAc:H₂O (67:10:23)=0.31 (SiO₂).

11. pGlu—Asn—Cys—Pro—Arg—Gly—NH₂.acetate 450 mg (0.40 millimol) of the peptide obtained in 10. were dissolved in a mixture of 12.5 ml of TFA, 0.13 ml of MeSO₃H and 0.01 ml of thioanisole and stirred for 5 hours. The reaction mixture was subsequently poured out into ether, resulting in an oil. The supernatant liquid was decanted and the oil was stirred twice with ether. The oil was subsequently dissolved in t.BuOH and H₂O (1:1) and subjected to exchange with an ion exchanger in the acetate form (Dowex 2X-8) and then freeze-dried.

Yield: 300 mg.

The freeze-dried material was dissolved in 10 ml of 50% strength HOAc and stirred for 6 hours at 50° C., after which it was again freeze-dried. The material was then purified by chromatography.

Yield: 84 mg.
Rf in 1-BuOH:HOAc:H₂O (2:1:1)=0.14 (SiO₂, Woelm).

EXAMPLE 2

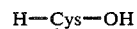

1. Z—Gln—Asn—Cys—Pro—Leu—Gly—NH₂.HCl 2.6 g (3 millimols) of Z-Gln-Asn-Cys(Scm)-Pro-Leu-Gly-NH₂ (prepared analogously to the method described in Example 1; Rf in CH₂Cl₂:MeOH 8:2=0.60 on SiO₂) were dissolved in 30 ml of DMF, after which 0.78 g (4.4 millimols) of H-Cys-OH.HCl.H₂O were added. After having been stirred for 2½ hours at room temperature, the reaction mixture was poured out into ether, causing the peptide to separate out as an oil. The oil was dissolved in a small amount of MeOH and purified on a (Sephadex) column, using methanol as the eluant.

Yield: 0.65 g (24%).
Rf=0.36 1-BuOH:HOAc:H₂O (4:1:1)=0.36 on SiO₂.

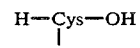

2. pGlu—Asn—Cys—Pro—Leu—Gly—NH₂.acetate 0.65 g (0.71 millimol) of the peptide obtained in 1. were dissolved in 75 ml of TFA, 1.2 ml of methanesulphonic acid and 0.25 ml of thioanisole. After the mixture had been stirred for 2 hours, 100 ml of ether were added, resulting in a precipitate. This precipitate was stirred twice with ether and decanted. The solid was then dissolved in t-BuOH:H₂O (1:1), subjected to exchange with Dowex 2X-8 Ac⁻ and then freeze-dried. The freeze-dried material was purified chromatographically (Merck type C ready-to-use column) with 1-BuOH:HOAc:H₂O (3:1:1) as eluant. The material obtained was then purified by Craig distribution, using 1-BuOH:HOAc:H₂O (4:1:5).

Yield: 137 mg (22%).

Rf in 1-BuOH:pyridine:HOAc:H₂O (8:3:1:4)=0.26 (SiO₂, Woelm).

EXAMPLE 3

1. 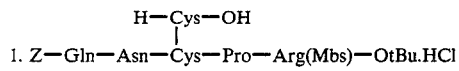 Z—Gln—Asn—Cys—Pro—Arg(Mbs)—OtBu.HCl
   |
   H—Cys—OH 2.2 g (2.06 millimols) of Z-Gln-Asn-Cys(Scm)-Pro-Arg(Mbs)-OtBu (obtained analogously to the method described in Example 1; Rf in CH₂Cl₂:MeOH:H₂O (70:30:5)=0.94 on SiO₂) were dissolved in 20 ml of MeOH, after which 0.35 g (1.96 millimols) of H-Cys-OH.H₂O.HCl were added with stirring and the mixture was stirred for 1 hour. A precipitate was obtained by adding 20 ml of ether. The liquid was decanted and the solid was stirred twice with 100 ml of ether. The solid was then dissolved in 200 ml of CH₂Cl₂ and extracted with 2×100 ml of water. The water layer was freeze-dried.

Yield: 1.85 g (74%).

Rf in CH₂Cl₂:MeOH:H₂O (70:30:5)=0.37 on SiO₂.

2. pGlu—Asn—Cys—Pro—Arg—OH.acetate
        |
        H—Cys—OH 180 mg (0.16 millimol) of the peptide obtained in 1. were dissolved in 3.7 ml of TFA, 0.37 ml of thio-anisole and 0.9 ml of methanesulphonic acid and the mixture was stirred for 5 hours at room temperature. Thereafter, the reaction mixture was poured out into 25 ml of ether and the precipitate obtained was filtered off and washed with ether. The solid was dissolved in t-BuOH and water (1:1) and subjected to exchange with an ion exchanger in the acetate form (Dowex 2X-8). The ion exchanger was filtered off and the solution was freeze-dried. The solid was then dissolved in 10 ml of 50% strength acetic acid, stirred for 5 hours at 50° C. and then again freeze-dried. This product was purified chromatographically (Merck ready-to-use column), using 1-BuOH:HOAc:H₂O (1:1:1) as the eluant.

Yield: 47 mg (40%).

Rf in 2-BuOH:Py:25% NH₃OH:H₂O (20:20:3:15)=0.21 (SiO₂).

EXAMPLE 4

Using a similar method to that described in Example 1.11,

Z—Gln—Asn—Cys—Pro—Leu—OtBu.HCl
        |
        H—Cys—OH (Rf in 1-BuOH:Py:HOAc:H₂O (8:3:1:4)=0.12) was converted to pGlu—Asn—Cys—Pro—Leu—OH
        |
        H—Cys—OH.acetate Rf in 1-BuOH:HOAc:H₂O (2:1:1)=0.40 (SiO₂).

EXAMPLE 5

The acetates of:

pGlu—Asn—Cys—Pro—Lys—Gly—OH
        |
        H—Cys—OH pGlu—Asn—Cys—Pro—Lys—OH
        |
        H—Cys—OH pGlu—Asn—Cys—Pro—Leu—OMe
        |
        H—Cys—OH pGlu—Asn—Cys—Pro—Leu—NH₂
        |
        H—Cys—OH are prepared in a similar manner.

EXAMPLE 6

1. (Z—Glu—Asn—Cys—Pro—Arg(Mbs)—OtBu)₂
              |

1.62 g (1.33 mmol) of Z-Glu-Asn-Cys(Trt)-Pro-Arg(Mbs)-OtBu (obtained analogously to the method described in Example 1; Rf in CHCl₃:MeOH:H₂O (70:30:5)=0.70 (SiO₂)) were dissolved in 292 ml of a 0.005M solution of iodine in acetic acid. After stirring during 1 hour at room temperature a sodium thiosulphate solution was slowly added till a pale yellow solution was obtained. Next 1.33 ml of a 1N NaOH solution and 250 ml of water were added and the resulting precipitate was removed by filtration and washed with water. Recrystallization was carried out in MeOH/ether.

Yield: 1.03 g (79%).

Rf in CH₂Cl₂:MeOH (8:2)=0.35 (SiO₂).

2. (pGlu—Asn—Cys—Pro—arg—OH)₂
              |

1.03 g (0.53 mmol) of the protected dimer described above were dissolved during stirring in 10 ml of TFA to which 6.1 g of methane sulphonic acid and 0.6 g of thioanisole were added. After standing during 5 hours at room temperature the solution was added dropwise to 100 ml of ether and the resulting precipitate was removed by filtration and washed with ether. Next the compound was dissolved in a 1:1 mixture of t.BuOH and H₂O exchanged using an ion exchanger in the acetate form (Dowex 2X-8) and freeze-dried. The freeze-dried material (690 mg) was dissolved in 10 ml of a 50% HOAc solution and maintained during 5 hours at 50° C. After freeze-drying the compound was purified chromatographically on a SiO₂ column with the elution system 1-BuOH:HOAc:H₂O (1:1:1).

Yield: 150 mg.

Rf in 1-BuOH:HOAc:H₂O (1:2:1)=0.42 (SiO₂, Woelm).

EXAMPLE 7

The compound Z-Glu-Asn-Cys(Trt)-Pro-Arg(Mbs)-Gly-NH₂ (obtained according to Example 1) was treated with I₂ in the way described in Example 6.1, whereafter the peptide

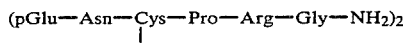

was obtained as described in Example 6.2.

Rf in 1-BuOH:HOAc:H₂O (1:2:1)=0.27 (SiO₂, Woelm).

EXAMPLE 8

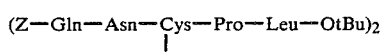

was prepared in a way analogous to Example 6.

0.7 g of this peptide was dissolved in 75 ml of TFA, 1.2 ml of methanesulphonic acid and 0.25 ml of thioanisole. After a 2 hours stirring period 100 ml of ether was added leading to the formation of a precipitate, which then was washed with ether. Thereafter the solid material was dissolved in t-BuOH:H₂O (1:1), exchanged with Dowex (2X-8 Ac⁻), and after being freeze-dried it was chromatographically purified on a SiO₂ column, yielding an acetate salt of

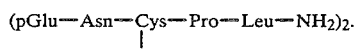

Rf in 1-BuOH:Py:HOAc:H₂O (8:3:1:4)=0.22 (SiO₂).

EXAMPLE 9

In a similar manner were prepared:

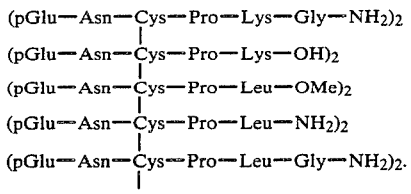

We claim:

1. A peptide having the general formula:

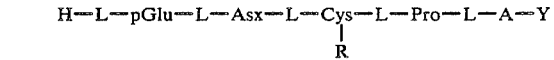

or a functional derivative thereof, wherein
R represents

A represents the amino acid radical Arg, Lys or Leu, and
Y represents the group -OH or -Gly-OH.

2. A peptide according to claim 1, having the formula:

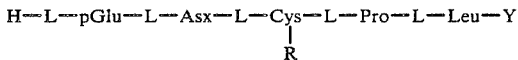

or a functional derivative thereof,
wherein R and Y have the meaning given in claim 1.

3. A peptide according to claim 1, having the formula:

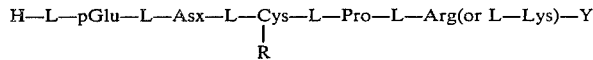

or a functional derivative thereof,
wherein R and Y have the meaning given in claim 1.

4. A pharmaceutical composition for effecting memory functions comprising an effective amount of a peptide according to any of claims 1–3 and a pharmaceutical acceptable carrier.

* * * * *